(12) United States Patent
Shikhman

(10) Patent No.: US 9,665,956 B2
(45) Date of Patent: May 30, 2017

(54) GRAPHICALLY BASED METHOD FOR DISPLAYING INFORMATION GENERATED BY AN INSTRUMENT

(75) Inventor: Menahem Shikhman, Miami, FL (US)

(73) Assignee: ABBOTT INFORMATICS CORPORATION, Hollywood, FL (US)

( * ) Notice: Subject to any disclaimer, the term of this patent is extended or adjusted under 35 U.S.C. 154(b) by 0 days.

(21) Appl. No.: 13/118,001

(22) Filed: May 27, 2011

(65) Prior Publication Data

US 2012/0299928 A1  Nov. 29, 2012

(51) Int. Cl.
G06T 11/20 (2006.01)
G06F 19/00 (2011.01)

(52) U.S. Cl.
CPC .......... *G06T 11/206* (2013.01); *G06F 19/366* (2013.01); *G06T 11/20* (2013.01)

(58) Field of Classification Search
CPC ....... G06F 19/366; G06T 11/20; G06T 11/206
USPC .................. 715/771, 830; 348/143
See application file for complete search history.

(56) References Cited

U.S. PATENT DOCUMENTS

| | | | |
|---|---|---|---|
| 4,812,996 A | 3/1989 | Stubbs | |
| 4,831,580 A | 5/1989 | Yamada | |
| 4,985,857 A | 1/1991 | Bajpai et al. | |
| 5,104,621 A | 4/1992 | Pfost et al. | |
| 5,314,825 A * | 5/1994 | Weyrauch | G01N 35/00663 356/246 |
| 5,366,896 A * | 11/1994 | Margrey | G01N 35/00871 422/105 |
| 5,532,941 A | 7/1996 | Lin | |
| 5,614,415 A | 3/1997 | Markin | |
| 5,664,093 A | 9/1997 | Barnett et al. | |
| 5,812,394 A | 9/1998 | Lewis et al. | |
| 5,920,718 A | 7/1999 | Uczekaj et al. | |

(Continued)

FOREIGN PATENT DOCUMENTS

| | | |
|---|---|---|
| CA | 2573232 A1 | 2/2006 |
| CA | 2594343 | 8/2006 |

(Continued)

OTHER PUBLICATIONS

Starlims Version 10 Configurable Off-the-Shelf LIMS for Laboratory and Enterprise Collaboration (Copyright 2008) available at starlims.com as of Mar. 28, 2010 ( See attached printout of http://web.archive.org/web/20100328051822/http://www.starlims.com/news/TechnicalNotes.htm).*

(Continued)

*Primary Examiner* — William Bashore
*Assistant Examiner* — Nathan Shrewsbury
(74) *Attorney, Agent, or Firm* — Klintworth & Rozenblatt IP LLC

(57) ABSTRACT

A computer readable memory medium comprising program instructions for graphically displaying information generated by an instrument is provided. The information is being displayed within a laboratory management system. The program instructions are executable by a processor to generate an instrument information representation in response to receiving information generated by an instrument and display the instrument information representation on a display. The instrument information representation visually presents the information generated by the instrument.

20 Claims, 8 Drawing Sheets

(56) References Cited

U.S. PATENT DOCUMENTS

| | | |
|---|---|---|
| 5,946,471 A | 8/1999 | Voorhees et al. |
| 5,985,670 A | 11/1999 | Markin |
| 6,055,487 A * | 4/2000 | Margery .......... G01N 35/00594 436/43 |
| 6,064,812 A | 5/2000 | Parthasarathy et al. |
| 6,094,684 A | 7/2000 | Pallmann |
| 6,102,965 A | 8/2000 | Dye et al. |
| 6,173,438 B1 | 1/2001 | Kodosky et al. |
| 6,192,320 B1 | 2/2001 | Margrey et al. |
| 6,219,628 B1 | 4/2001 | Kodosky et al. |
| 6,298,474 B1 | 10/2001 | Blowers et al. |
| 6,326,147 B1 | 12/2001 | Oldham et al. |
| 6,370,569 B1 | 4/2002 | Austin |
| 6,526,566 B1 | 2/2003 | Austin |
| 6,581,012 B1 * | 6/2003 | Aryev ................ G01N 35/0092 702/22 |
| 6,643,691 B2 | 11/2003 | Austin |
| 6,681,198 B2 | 1/2004 | Buote et al. |
| 6,751,653 B2 | 6/2004 | Austin |
| 6,879,926 B2 | 4/2005 | Schmit et al. |
| 6,909,974 B2 | 6/2005 | Yung et al. |
| 6,938,026 B2 | 8/2005 | Yundt-Pacheco |
| 7,000,191 B2 | 2/2006 | Schmitt et al. |
| 7,162,387 B2 | 1/2007 | Johnson et al. |
| 7,197,418 B2 | 3/2007 | Fuller, III et al. |
| 7,197,743 B2 | 3/2007 | Borg et al. |
| 7,200,838 B2 | 4/2007 | Kodosky et al. |
| 7,275,070 B2 | 9/2007 | Kataria et al. |
| 7,275,235 B2 | 9/2007 | Molinari et al. |
| 7,333,962 B2 | 2/2008 | Zen |
| 7,379,821 B2 * | 5/2008 | Yung et al. .................... 702/19 |
| 7,379,823 B2 | 5/2008 | Yung et al. |
| 7,467,153 B2 | 12/2008 | Boyce et al. |
| 7,491,367 B2 | 2/2009 | Yung et al. |
| 7,499,824 B2 | 3/2009 | Johnson et al. |
| 7,506,304 B2 | 3/2009 | Morrow et al. |
| 7,512,931 B2 | 3/2009 | Schmit |
| 7,536,269 B2 | 5/2009 | Sierer et al. |
| 7,565,351 B1 | 7/2009 | Callaghan |
| 7,574,690 B2 | 8/2009 | Shah et al. |
| 7,581,191 B2 | 8/2009 | Rice et al. |
| 7,593,787 B2 | 9/2009 | Feingold et al. |
| 7,593,944 B2 | 9/2009 | Rogers et al. |
| 7,594,220 B2 | 9/2009 | Kodosky et al. |
| 7,594,226 B2 | 9/2009 | Stelzer et al. |
| 7,603,478 B2 | 10/2009 | Thurman et al. |
| 7,603,652 B2 | 10/2009 | Makowski et al. |
| 7,606,950 B2 | 10/2009 | Breyer |
| 7,607,070 B2 | 10/2009 | Clark et al. |
| 7,613,954 B2 | 11/2009 | Grey et al. |
| 7,620,459 B2 | 11/2009 | Renner |
| 7,620,897 B2 | 11/2009 | Shah et al. |
| 7,624,294 B2 | 11/2009 | Conway |
| 7,624,375 B2 | 11/2009 | Santori et al. |
| 7,626,474 B2 | 12/2009 | Mullen et al. |
| 7,627,695 B2 | 12/2009 | Peck et al. |
| 7,627,860 B2 | 12/2009 | Kodosky et al. |
| 7,630,560 B2 | 12/2009 | Wenzel |
| 7,630,854 B2 | 12/2009 | Sierer et al. |
| 7,631,097 B2 | 12/2009 | Moch et al. |
| 7,631,295 B2 | 12/2009 | Makowski et al. |
| 7,644,207 B2 | 1/2010 | Castro et al. |
| 7,647,562 B2 | 1/2010 | Ghercioiu et al. |
| 7,647,578 B2 | 1/2010 | Murphy et al. |
| 7,647,600 B2 | 1/2010 | Müller et al. |
| 7,649,726 B2 | 1/2010 | Castro |
| 7,650,264 B2 | 1/2010 | Kodosky et al. |
| 7,650,316 B2 | 1/2010 | Peck et al. |
| 7,650,574 B2 | 1/2010 | Nattinger |
| 7,650,589 B2 | 1/2010 | Cifra |
| 7,650,594 B2 | 1/2010 | Nattinger |
| 7,668,376 B2 | 2/2010 | Lin et al. |
| 7,669,185 B2 | 2/2010 | Vrancic et al. |
| 7,680,605 B2 | 3/2010 | Yung et al. |
| 7,684,878 B2 | 3/2010 | Reindel et al. |
| 7,689,727 B2 | 3/2010 | Chandhoke |
| 7,689,917 B2 | 3/2010 | Washington et al. |
| RE41,228 E | 4/2010 | Kodosky et al. |
| 7,694,273 B2 | 4/2010 | Kodosky et al. |
| 7,701,869 B2 | 4/2010 | Hogan |
| 7,702,416 B2 | 4/2010 | Ravish et al. |
| 7,702,417 B2 | 4/2010 | Ravish et al. |
| 7,703,027 B2 | 4/2010 | Hsu et al. |
| 7,703,032 B2 | 4/2010 | Wells |
| 7,703,034 B2 | 4/2010 | Kornerup et al. |
| 7,707,014 B2 | 4/2010 | Kodosky et al. |
| 7,725,356 B2 | 5/2010 | Shah et al. |
| 7,725,627 B2 | 5/2010 | Crain, II et al. |
| 7,725,874 B2 | 5/2010 | Kornerup et al. |
| 7,725,877 B2 | 5/2010 | Andrade et al. |
| 7,730,450 B2 | 6/2010 | Mercer |
| 7,743,335 B2 | 6/2010 | Rogers et al. |
| 7,743,362 B2 | 6/2010 | Peck et al. |
| 7,760,238 B2 | 7/2010 | Giesen |
| 7,761,802 B2 | 7/2010 | Shah et al. |
| 7,761,846 B2 | 7/2010 | Hayles |
| 7,761,847 B2 | 7/2010 | Kornerup et al. |
| 7,761,859 B2 | 7/2010 | Low |
| 7,764,619 B2 | 7/2010 | Mathena et al. |
| 7,765,278 B2 | 7/2010 | Dove et al. |
| 7,765,493 B2 | 7/2010 | Chickles et al. |
| 7,769,597 B2 | 8/2010 | Fry et al. |
| 7,778,717 B2 | 8/2010 | Bachman et al. |
| 7,791,671 B2 | 9/2010 | Schultz et al. |
| 7,793,273 B2 | 9/2010 | Mercer et al. |
| 7,801,258 B2 | 9/2010 | Narus et al. |
| 7,802,229 B2 | 9/2010 | Kornerup et al. |
| 8,574,564 B2 * | 11/2013 | Renner ................ A61K 39/39 424/93.2 |
| 2002/0109722 A1 | 8/2002 | Rogers et al. |
| 2002/0111783 A1 | 8/2002 | Kodosky et al. |
| 2002/0156792 A1 * | 10/2002 | Gombocz ......... G06F 17/30286 |
| 2002/0174264 A1 | 11/2002 | Fuller et al. |
| 2002/0184326 A1 | 12/2002 | Thomson |
| 2002/0196282 A1 | 12/2002 | Washington et al. |
| 2003/0036866 A1 | 2/2003 | Nair et al. |
| 2003/0144997 A1 | 7/2003 | Hugley |
| 2003/0145252 A1 | 7/2003 | Grey et al. |
| 2003/0145280 A1 | 7/2003 | Grey et al. |
| 2003/0165259 A1 | 9/2003 | Balent et al. |
| 2003/0172127 A1 | 9/2003 | Northrup et al. |
| 2003/0177042 A1 | 9/2003 | Leon |
| 2003/0177471 A1 | 9/2003 | Chiu et al. |
| 2003/0228583 A1 * | 12/2003 | Amacher et al. ................. 435/6 |
| 2004/0017392 A1 | 1/2004 | Welch |
| 2004/0031019 A1 | 2/2004 | Lamanna et al. |
| 2004/0032412 A1 | 2/2004 | Odom |
| 2004/0032430 A1 * | 2/2004 | Yung et al. .................... 345/771 |
| 2004/0034478 A1 | 2/2004 | Yung et al. |
| 2004/0039531 A1 | 2/2004 | Yung et al. |
| 2004/0042471 A1 * | 3/2004 | Yung et al. .................... 370/401 |
| 2004/0093180 A1 | 5/2004 | Grey et al. |
| 2004/0122708 A1 | 6/2004 | Avinash et al. |
| 2004/0150667 A1 | 8/2004 | Dove et al. |
| 2004/0205111 A1 | 10/2004 | Chasmawala et al. |
| 2004/0230945 A1 | 11/2004 | Bryant et al. |
| 2005/0013736 A1 | 1/2005 | McKeever |
| 2005/0022103 A1 | 1/2005 | Yundt-Pacheco |
| 2005/0028107 A1 | 2/2005 | Gomes et al. |
| 2005/0028138 A1 | 2/2005 | Case et al. |
| 2005/0038676 A1 * | 2/2005 | Showalter et al. ............... 705/2 |
| 2005/0049814 A1 | 3/2005 | Ramchandani |
| 2005/0070019 A1 | 3/2005 | Yamamoto |
| 2005/0076002 A1 | 4/2005 | Williams et al. |
| 2005/0106736 A1 | 5/2005 | Yung et al. |
| 2005/0149566 A1 | 7/2005 | Baek et al. |
| 2005/0155014 A1 | 7/2005 | Andrade et al. |
| 2005/0155015 A1 | 7/2005 | Novacek |
| 2005/0177816 A1 | 8/2005 | Kudukoli et al. |
| 2005/0195194 A1 | 9/2005 | Cummings |
| 2005/0228608 A1 | 10/2005 | Wells |
| 2005/0257195 A1 | 11/2005 | Morrow et al. |
| 2005/0268173 A1 | 12/2005 | Kudukoli et al. |
| 2006/0008151 A1 | 1/2006 | Lin et al. |

(56) References Cited

U.S. PATENT DOCUMENTS

| | | |
|---|---|---|
| 2006/0036656 A1 | 2/2006 | Mercer |
| 2006/0036799 A1 | 2/2006 | Shah et al. |
| 2006/0036997 A1 | 2/2006 | Low |
| 2006/0041860 A1 | 2/2006 | Carmichael et al. |
| 2006/0063265 A1 | 3/2006 | Welcher et al. |
| 2006/0088940 A1 | 4/2006 | Feingold et al. |
| 2006/0117302 A1 | 6/2006 | Mercer et al. |
| 2006/0156294 A1 | 7/2006 | Fuller, III et al. |
| 2006/0168183 A1 | 7/2006 | Fuller, III et al. |
| 2006/0168515 A1 | 7/2006 | Dorsett, Jr. et al. |
| 2006/0190105 A1 | 8/2006 | Hsu et al. |
| 2006/0225034 A1 | 10/2006 | Peck et al. |
| 2006/0291399 A1 | 12/2006 | Mathena et al. |
| 2007/0010911 A1 | 1/2007 | Feingold et al. |
| 2007/0038592 A1 | 2/2007 | Haub et al. |
| 2007/0044030 A1 | 2/2007 | Hayles |
| 2007/0044072 A1 | 2/2007 | Hayles |
| 2007/0044073 A1 | 2/2007 | Kornerup et al. |
| 2007/0044078 A1 | 2/2007 | Cifra |
| 2007/0088865 A1 | 4/2007 | Breyer |
| 2007/0089063 A1 | 4/2007 | Breyer |
| 2007/0129818 A1 | 6/2007 | Andrade et al. |
| 2007/0129894 A1 | 6/2007 | Yung et al. |
| 2007/0141711 A1 | 6/2007 | Stephens et al. |
| 2007/0168943 A1 | 7/2007 | Marini et al. |
| 2007/0179644 A1 | 8/2007 | Ravish et al. |
| 2007/0185828 A1* | 8/2007 | Brown .................. 707/1 |
| 2007/0198445 A1 | 8/2007 | Zen |
| 2007/0214427 A1 | 9/2007 | Peck et al. |
| 2007/0233655 A1 | 10/2007 | Engels |
| 2007/0234195 A1 | 10/2007 | Wells |
| 2007/0244990 A1 | 10/2007 | Wells |
| 2007/0282997 A1 | 12/2007 | Trochman |
| 2007/0297443 A1 | 12/2007 | Bowers et al. |
| 2008/0022264 A1 | 1/2008 | Macklem et al. |
| 2008/0022270 A1 | 1/2008 | Morrow et al. |
| 2008/0034298 A1 | 2/2008 | Kodosky et al. |
| 2008/0034300 A1 | 2/2008 | Shah et al. |
| 2008/0034345 A1 | 2/2008 | Curtis et al. |
| 2008/0043826 A1 | 2/2008 | Castro et al. |
| 2008/0046414 A1 | 2/2008 | Haub et al. |
| 2008/0050280 A1 | 2/2008 | Fujita |
| 2008/0052665 A1 | 2/2008 | Bray |
| 2008/0059944 A1 | 3/2008 | Patterson et al. |
| 2008/0096495 A1 | 4/2008 | Shen |
| 2008/0168850 A1 | 7/2008 | Fischer |
| 2008/0177612 A1* | 7/2008 | Starink ............ G06Q 10/06316 705/7.26 |
| 2008/0240321 A1 | 10/2008 | Narus et al. |
| 2008/0256511 A1 | 10/2008 | Lay et al. |
| 2008/0263343 A1 | 10/2008 | Kassas et al. |
| 2008/0263468 A1 | 10/2008 | Cappione et al. |
| 2008/0263515 A1 | 10/2008 | Dellas et al. |
| 2008/0263521 A1 | 10/2008 | Neumann et al. |
| 2008/0270920 A1 | 10/2008 | Hudson |
| 2008/0300697 A1 | 12/2008 | Moriat et al. |
| 2008/0307332 A1 | 12/2008 | Hayles et al. |
| 2008/0312893 A1 | 12/2008 | Denton |
| 2009/0019065 A1 | 1/2009 | Sapounas |
| 2009/0019453 A1 | 1/2009 | Kodaganur et al. |
| 2009/0027509 A1 | 1/2009 | Giesen |
| 2009/0049424 A1 | 2/2009 | Kumar et al. |
| 2009/0089715 A1 | 4/2009 | Dickey |
| 2009/0099862 A1 | 4/2009 | Fireman et al. |
| 2009/0106755 A1 | 4/2009 | Chandhoke |
| 2009/0106761 A1 | 4/2009 | Chandhoke |
| 2009/0113322 A1 | 4/2009 | Rogers |
| 2009/0113337 A1 | 4/2009 | Rogers |
| 2009/0117620 A1 | 5/2009 | Fritchie et al. |
| 2009/0121908 A1 | 5/2009 | Regier |
| 2009/0130765 A1 | 5/2009 | Bauer et al. |
| 2009/0178025 A1 | 7/2009 | Morrow et al. |
| 2009/0192363 A1* | 7/2009 | Case .................... G06F 19/322 600/300 |
| 2009/0193396 A1 | 7/2009 | Hartadinata |
| 2009/0199052 A1 | 8/2009 | Yamaguchi et al. |
| 2009/0234471 A1 | 9/2009 | Chandhoke |
| 2009/0235231 A1 | 9/2009 | Kodosky et al. |
| 2009/0241068 A1 | 9/2009 | Page et al. |
| 2009/0241069 A1 | 9/2009 | Fuller, III et al. |
| 2009/0259427 A1 | 10/2009 | Hirayama |
| 2009/0288025 A1 | 11/2009 | King et al. |
| 2009/0288073 A1 | 11/2009 | Gosalia et al. |
| 2009/0292511 A1 | 11/2009 | Vrancic et al. |
| 2009/0293044 A1 | 11/2009 | Boettcher et al. |
| 2009/0297042 A1 | 12/2009 | Nair et al. |
| 2009/0299924 A1 | 12/2009 | Bauer et al. |
| 2009/0316977 A1 | 12/2009 | Juncker et al. |
| 2009/0319987 A1 | 12/2009 | Bartz |
| 2010/0010646 A1 | 1/2010 | Drew et al. |
| 2010/0010746 A1 | 1/2010 | Ariyoshi et al. |
| 2010/0023866 A1 | 1/2010 | Peck et al. |
| 2010/0030509 A1 | 2/2010 | Crain, II et al. |
| 2010/0030539 A1 | 2/2010 | Chandhoke et al. |
| 2010/0031231 A1 | 2/2010 | Ilic et al. |
| 2010/0049542 A1 | 2/2010 | Benjamin et al. |
| 2010/0058289 A1 | 3/2010 | Hudson, III et al. |
| 2010/0064374 A1 | 3/2010 | Martin et al. |
| 2010/0070906 A1 | 3/2010 | Hishikawa |
| 2010/0114501 A1 | 5/2010 | Kondou et al. |
| 2010/0138231 A1 | 6/2010 | Linthicum et al. |
| 2010/0223556 A1 | 9/2010 | Wakabayashi et al. |
| 2010/0271479 A1* | 10/2010 | Heydlauf .................. 348/143 |
| 2010/0287477 A1 | 11/2010 | Maetzler et al. |
| 2011/0169836 A1 | 7/2011 | Orihashi et al. |
| 2011/0213700 A1* | 9/2011 | Sant'Anselmo .............. 705/39 |
| 2011/0223077 A1 | 9/2011 | Tanaka et al. |
| 2011/0235873 A1 | 9/2011 | Jaffe et al. |
| 2011/0244558 A1 | 10/2011 | Hamada et al. |
| 2011/0244580 A1 | 10/2011 | Hamada et al. |
| 2011/0245089 A1 | 10/2011 | Scott et al. |
| 2012/0038651 A1 | 2/2012 | Case et al. |
| 2012/0041777 A1 | 2/2012 | Case et al. |
| 2012/0042214 A1 | 2/2012 | Jacobs et al. |
| 2012/0203510 A1* | 8/2012 | Perez .................... G01J 3/0264 702/189 |

FOREIGN PATENT DOCUMENTS

| | | |
|---|---|---|
| CN | 101042822 A | 9/2007 |
| CN | 101359223 A | 2/2009 |
| CN | 102413027 A | 4/2012 |
| CN | 202533939 U | 11/2012 |
| CN | 202650175 U | 1/2013 |
| DE | 102009058596 A1 | 6/2011 |
| DE | 102012102918 A1 | 10/2013 |
| EP | 1457913 A3 | 4/2005 |
| EP | 1331874 B1 | 8/2009 |
| GB | 2477799 A | 8/2011 |
| JP | 2008020309 A | 1/2008 |
| JP | 2009162584 A | 7/2009 |
| JP | 2012078264 A | 4/2012 |
| JP | 2012225902 A | 11/2012 |
| KR | 1032973 B1 | 5/2011 |

OTHER PUBLICATIONS

United States Patent and Trademark Office (International Searching Authority), International Search Report and Written Opinion for PCT/US 12/36281 (Filing date May 3, 2012) Date of Mailing: Jun. 20, 2012.

Starlims Clinical Solutions User Manual for V10; Starlims Database 10.5, Starlims Dictionary 10.5; Starlims.net XFD Framework Version 10.5.0.48, Starlims Corporation Jun. 2010 (pp. 1-490).

* cited by examiner

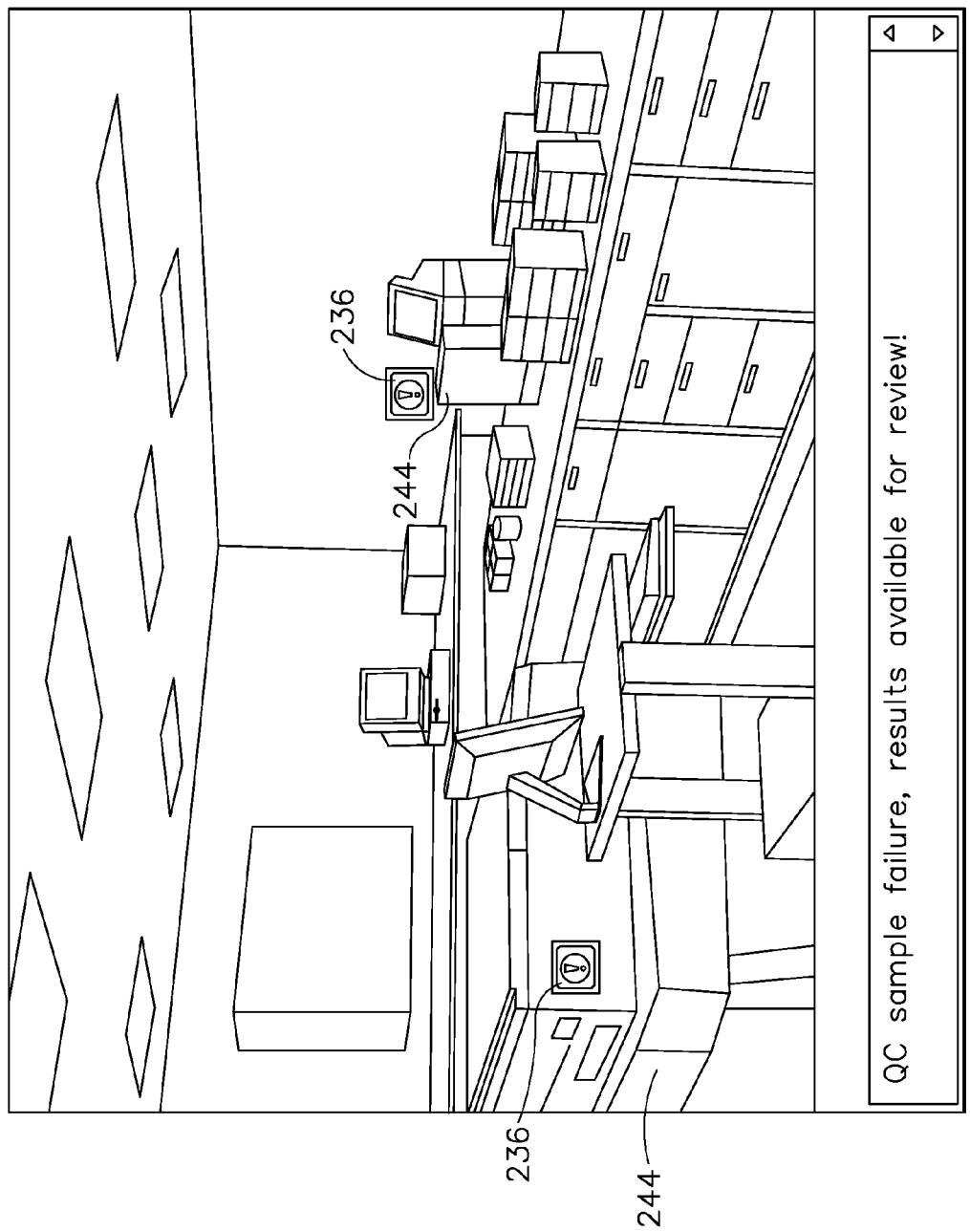

| Run # | QC Material | Level | Modula... | Result | Final | Units | Result Stat... | Approval Status | Expiration S... | WG Rules |
|---|---|---|---|---|---|---|---|---|---|---|
| | QC Material MULTILEVEL | | | | | | | | | |
| 5 | MULTILEVEL | Level 2 | | 35 | 35 | mg/dL | Done | Released | PASS | |
| 5 | MULTILEVEL | Level 1 | | 12 | 12 | mg/dL | Done | Released | PASS | |
| 4 | MULTILEVEL | Level 2 | | 33 | 33 | mg/dL | Done | Released | PASS | |
| 4 | MULTILEVEL | Level 1 | | 13 | 13 | mg/dL | Warning | Released | PASS | 1-2S |
| 3 | MULTILEVEL | Level 2 | | 35 | 35 | mg/dL | Done | Released | PASS | |
| 3 | MULTILEVEL | Level 1 | | 15 | 15 | mg/dL | ☐ Failed | Released | PASS | 1-3S |
| 2 | MULTILEVEL | Level 2 | | 32 | 32 | mg/dL | Done | Released | PASS | |
| 2 | MULTILEVEL | Level 1 | | 12 | 12 | mg/dL | Done | Released | PASS | |
| 1 | MULTILEVEL | Level 2 | | 30 | 30 | mg/dL | Done | Released | PASS | |
| 1 | MULTILEVEL | Level 1 | | 35 | 35 | mg/dL | Done | Released | PASS | |

Fig. 7

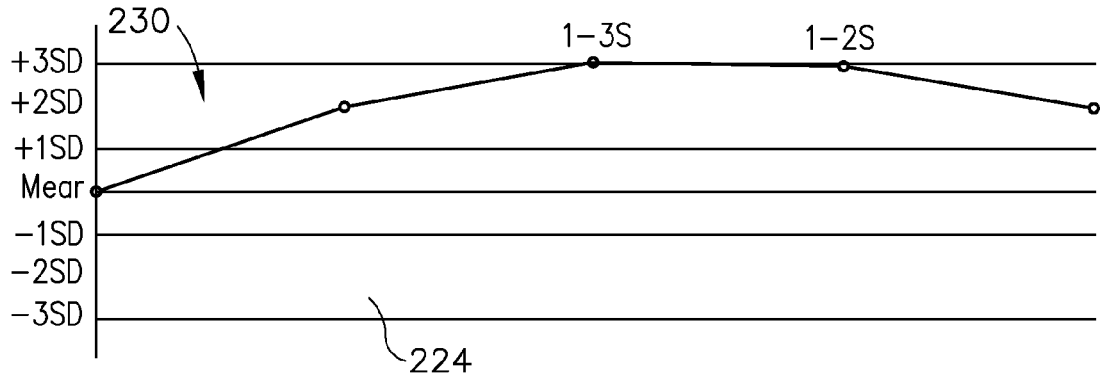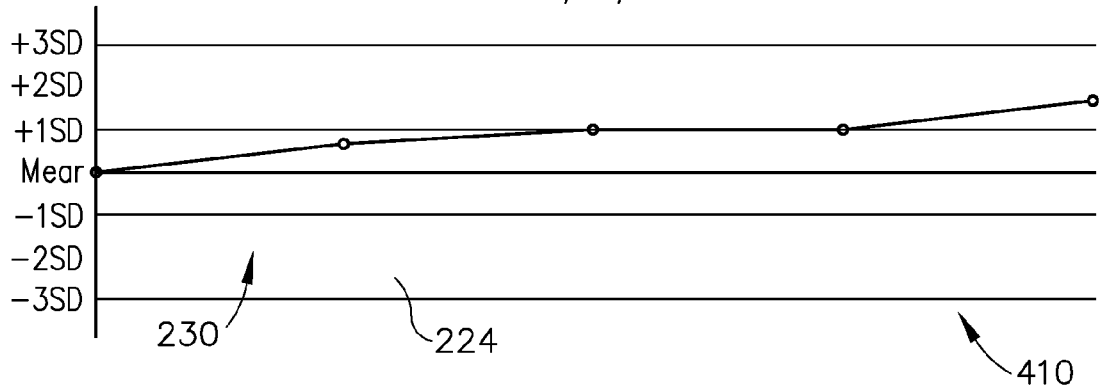
Fig.8

GRAPHICALLY BASED METHOD FOR DISPLAYING INFORMATION GENERATED BY AN INSTRUMENT

FIELD OF THE INVENTION

The present invention relates generally to a method for displaying information generated by an instrument in a laboratory. In particular, the invention relates to a graphically based method for displaying the status of an instrument in a laboratory and quality control results obtained from an instrument in a laboratory.

BACKGROUND

Laboratories use a variety of laboratory management systems to integrate laboratory software and instruments; to manage samples, laboratory users, and standards; to control other laboratory functions such as Quality Assurance (QA) and Quality Control (QC); to conduct sample planning, invoicing, and plate management; and to manage workflow. Laboratory management systems can include a variety of different types of systems for managing samples, information and/or instruments within a laboratory, such as a Laboratory Information System (LIS), a Process Development Execution System (PDES), and a Laboratory Information Management System or Laboratory Integration Management Solution (LIMS).

A Laboratory Information System ("LIS") is a class of software that receives, processes, and stores information generated by medical laboratory processes. LIS systems often must interface with instruments and other information systems such as hospital information systems (HIS).

A Process Development Execution System (PDES) is a system which is used by companies to perform development activities for manufacturing processes.

A Laboratory Information Management System or Laboratory Integration Management Solution (LIMS) is a software system used in laboratories for the integration of laboratory software and instruments and the management of samples, laboratory users, standards and other laboratory functions such as Quality Assurance (QA) and Quality Control (QC), sample planning, invoicing, plate management, and workflow automation. LIMS systems may also support information gathering, decision making, calculation, review and release into the workplace and away from the office. More recently, LIMS systems are starting to expand into Electronic Laboratory Notebooks, assay data management, data mining and data analysis.

Modern laboratory management systems have implemented extensive configurability as each laboratories needs for tracking additional data points can vary widely. Vendors of laboratory management systems often cannot make assumptions about what these data tracking needs are and therefore need to be adaptable to each environment. Users of laboratory management systems may also have regulatory concerns to comply with such as CLIA, HIPAA, GLP, ISO 17025, ASCLD Supplement, and FDA specifications and this can affect certain aspects of sample management in a laboratory management system. One key to compliance with many of these standards is audit logging of all changes to data of laboratory management systems, and in some cases a full electronic signature system is required for rigorous tracking of field level changes to data of laboratory management systems.

Laboratory management systems may be customized for use in a wide variety of settings and laboratories, such as medical or clinical laboratories, biological laboratories, chemistry laboratories, chemical or petroleum laboratories, commercial or manufacturing use, forensics or crime laboratories, pathology laboratories, public safety and public health laboratories, and water processing and testing facilities.

A user may configure a laboratory management system whereby users are assigned roles or groups. Typically the role of a user will dictate their access to specific data records in the laboratory management systems. Each user account is protected by security mechanisms such as a user id and a password. Users may have customized interfaces based on their role in the organization. For example, a laboratory manager might have full access to all of a laboratory management system's functions and data, whereas technicians might have access only to data and functionality needed for their individual work-tasks.

Some laboratory management systems offer some capability for integration with instruments. A laboratory management system may create control files that are "fed" into the instrument and direct its operation on some physical item such as a sample tube or sample plate. The laboratory management system may then receive information generated by the instrument and extract QC information, results information, or status information for assessment of the operation on the sample or samples. Data owners may access the resulting stored information at any time.

As instruments are being operated, instrument status may change from being in a first operating state to being in a second operating state. The instrument status of an instrument describes what operating state an instrument is operating within. Operating states describe the current operation of an instrument and include things such as an initialization state where the instrument is initialized upon powering on the instrument, an on state where the instrument is powered on and initialized, an off state where the instrument is powered off, a restart state where the instrument is restarted after being in the on state, a pause state where the instrument is in the on state but not receiving or generating information, a clear queue state where the instrument clears its memory of some or all received commands, and a usage state where the instrument is in use and conducting a task or performing a test. As the instrument status changes, the instrument generates instrument status information to indicate the current instrument status of an instrument. Additionally, as the instrument is being operated throughout the day, the instrument generates QC information for QC samples. All QC samples are grouped by lot number of the QC as well as level (i.e. high or low).

As instruments are being used and accessed within a laboratory, often times their instrument status is unknown to a user of the laboratory management system. As a result, the user is often unaware if an instrument within a laboratory is available for use or not. It would be desirable to provide a user with a graphical representation of the status an instrument within the laboratory management system and displayed on a display so that the user can visually and quickly check the status of an instrument. Additionally, it would be desirable to provide a user with information presented in a graphical manner which details how often an instrument is in or not in a particular state, for example how long an instrument in being used and therefore in the usage state. Additionally, it would be desirable to provide a user with information presented in a graphical manner which details the QC results of a particular instrument.

SUMMARY

In one aspect, a computer readable memory medium comprising program instructions for graphically displaying information generated by an instrument is provided. The information is being displayed within a laboratory management system. The program instructions are executable by a processor to generate an instrument information representation in response to receiving information generated by an instrument and display the instrument information representation on a display. The instrument information representation visually presents the information generated by the instrument.

In one aspect a method for graphically displaying information generated by an instrument is provided. The information is being displayed within a laboratory management system. The method includes generating an instrument information representation in response to receiving information generated by an instrument and displaying the instrument information representation on a display. The instrument information representation visually presents the information generated by the instrument.

In one aspect, a laboratory management system is provided. The laboratory management system includes a computer readable memory medium and at least one processor operable to access from the computer readable memory medium program instructions. The program instructions are executable by the processor to generate an instrument information representation in response to receiving information generated by an instrument and to display the instrument information representation on a display. The instrument information representation visually presents the information generated by the instrument.

The scope of the present invention is defined solely by the appended claims and is not affected by the statements within this summary.

BRIEF DESCRIPTION OF THE DRAWINGS

The invention can be better understood with reference to the following drawings and description. The components in the figures are not necessarily to scale, emphasis instead being placed upon illustrating the principles of the invention.

FIGS. 4-8 depict various states of a graphical display module displaying an instrument information representation which visually presents the information generated by the instrument, in accordance with one embodiment of the present invention.

DETAILED DESCRIPTION

The present invention makes use of the discovery that by providing a user with software which can generate an instrument information representation in response to receiving information generated by an instrument and display the instrument information representation on a display, users laboratory management systems may visually and quickly check the status of an instrument and may see information presented in a graphical manner which details the QC results of a particular instrument.

In the description that follows, the subject matter of the application will be described with reference to acts and symbolic representations of operations that are performed by one or more computers, unless indicated otherwise. As such, it will be understood that such acts and operations, which are at times referred to as being computer-executed, include the manipulation by the processing unit of the computer of electrical signals representing data in a structured form. This manipulation transforms the data or maintains it at locations in the memory system of the computer which reconfigures or otherwise alters the operation of the computer in a manner well understood by those skilled in the art. The data structures where data is maintained are physical locations of the memory that have particular properties defined by the format of the data. However, although the subject matter of the application is being described in the foregoing context, it is not meant to be limiting as those skilled in the art will appreciate that some of the acts and operations described hereinafter can also be implemented in hardware, software, and/or firmware and/or some combination thereof.

Figure 1:
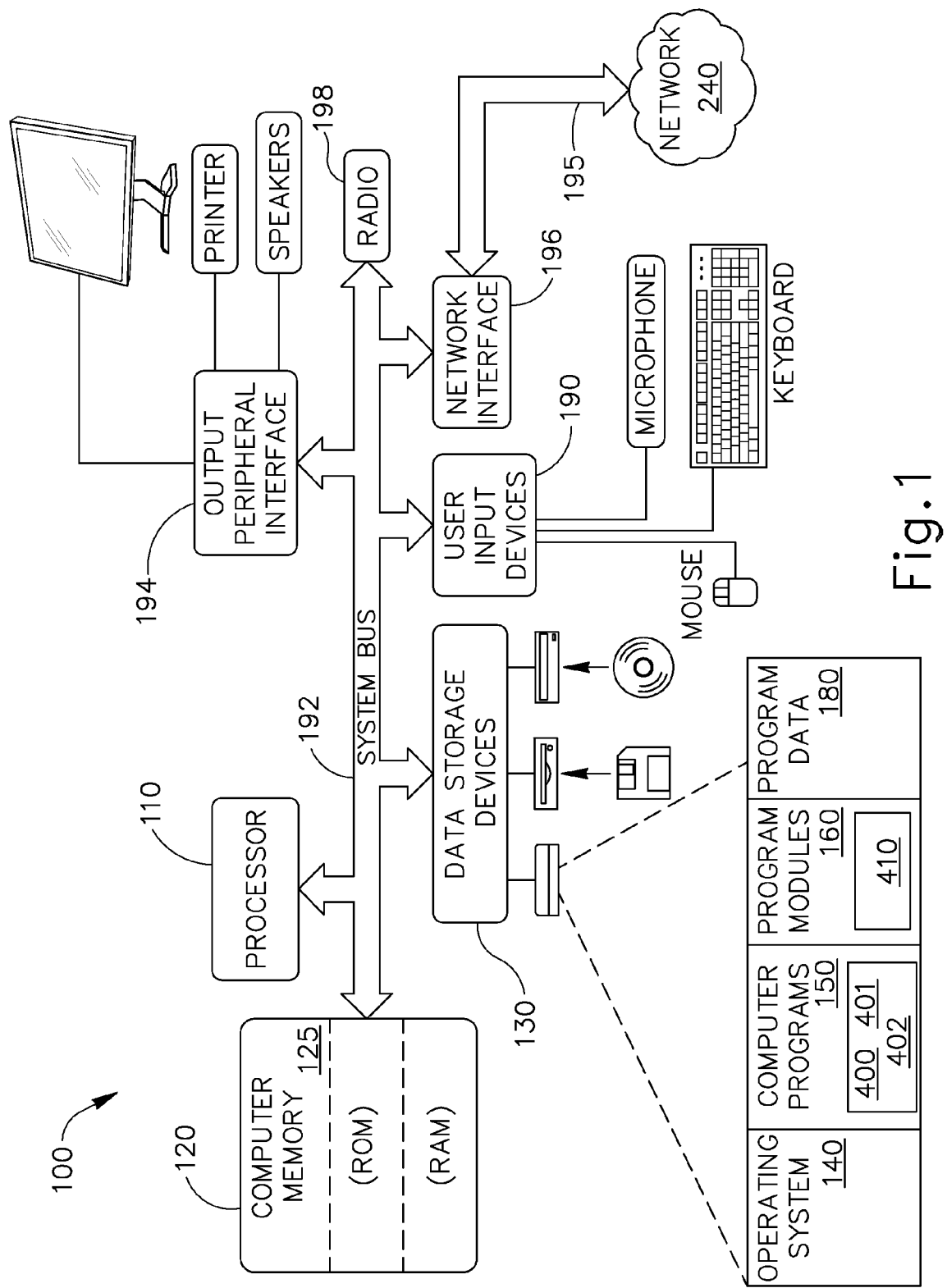
FIG. 1 depicts a block schematic diagram of an exemplary computing system, in accordance with one embodiment of the present invention.

With reference to FIG. 1, depicted is an exemplary computing system for implementing embodiments. FIG. 1 includes computer 100 running a computer program 150, such as a laboratory management system (LMS) software application 400. The LMS software application 400 includes software applications such as a Laboratory Information Management System (LIMS) software application 401, a Laboratory Information System (LIS) software application 402, or a Process Development Execution System (PDES) software application 403.

The LIMS software application 401 is a software application used in laboratories for the integration of laboratory software and instruments and the management of samples, laboratory users, standards and other laboratory functions such as Quality Assurance (QA) and Quality Control (QC), sample planning, invoicing, plate management, and workflow automation. The LIS software application 402 is a software application that receives, processes, and stores information generated by medical laboratory processes. The LIS software application 402 often must interface with instruments and other information systems such as hospital information systems (HIS). The LIS software application 402 is a highly configurable application which is customized to facilitate a wide variety of laboratory workflow models. The PDES software application 403 is a software application which is used by companies to perform development activities for manufacturing processes.

The computer 100 includes a processor 110 in communication with a computer readable memory medium 120. Computer readable memory medium 120 is any medium which can be used to store information which can later be accessed by processor 110. Computer readable memory medium 120 includes computer memory 125 and data storage devices 130. Computer memory 120 is preferably a fast-access memory and is used to run program instructions executable by the processor 110. Computer memory 120 includes random access memory (RAM), flash memory, and read only memory (ROM). Data storage devices 130 are preferably physical devices and are used to store any information or computer program which may be accessed by the processor 110, such as an operating system 140, computer programs 150 such as LMS software application 400, program modules 160 such as a graphical display module 410 which runs as a part of LMS software application 400, and program data 180. Data storage devices 130 and their associated computer readable memory medium provide storage of computer readable instructions, data structures, program modules and other data for the computer 100. Data storage devices 130 include magnetic medium like a floppy disk, a hard disk drive, and magnetic tape; an optical medium like a Compact Disc (CD), a Digital Video Disk (DVD), and a Blu-ray Disc; and solid state memory such as random access memory (RAM), flash memory, and read only memory (ROM).

Computer 100 further includes input devices 190 through which data may enter the computer 100, either automatically or by a user who enters commands and data. Input devices 190 can include an electronic digitizer, a flatbed scanner, a barcode reader, a microphone, a camera, a video camera, a keyboard and a pointing device, commonly referred to as a mouse, a trackball or a touch pad, a pinpad, any USB device, any Bluetooth enabled device, an RFID or NFC device, and a debit card reader. Other input devices may include a joystick, game pad, satellite dish, scanner, an instrument, a sensor, and the like. In one or more embodiments, input devices 190 are portable devices that can direct display or instantiation of applications running on processor 110.

These and other input devices 190 can be connected to processor 110 through a user input interface that is coupled to a system bus 192, but may be connected by other interface and bus structures, such as a parallel port, game port or a universal serial bus (USB). Computers such as computer 100 may also include other peripheral output devices such as speakers, printers, and/or display devices, which may be connected through an output peripheral interface 194 and the like.

Computer 100 also includes a radio 198 or other type of communications device for wirelessly transmitting and receiving data for the computer 100 with the aid of an antenna. Radio 198 may wirelessly transmit and receive data using WiMAX™, 802.11a/b/g/n, Bluetooth™, 2G, 2.5G, 3G, and 4G, wireless standards.

Computer 100 may operate in a networked environment 195 using logical connections to one or more remote computers, such as a remote server 240. The remote server 240 may be a personal computer, a server, a router, a network PC, a peer device or other common network node, and may include many if not all of the elements described above relative to computer 100. Networking environments are commonplace in offices, enterprise-wide computer networks, intranets and the Internet. For example, in the subject matter of the present application, computer 100 may comprise the source machine from which data is being migrated, and the remote computer may comprise the destination machine. Note, however, that source and destination machines need not be connected by a network or any other means, but instead, data may be migrated via any media capable of being written by the source platform and read by the destination platform or platforms. When used in a LAN or WLAN networking environment, computer 100 is connected to the LAN or WLAN through a network interface 196 or an adapter. When used in a WAN networking environment, computer 100 may include a modem or other means for establishing communications over the WAN, such as radio 198, to environments such as the Internet or to another remote computer. It will be appreciated that other means of establishing a communications link between computer 100 and other remote computers may be used.

In one embodiment, computer 100 is in communication with remote server 240, and the LMS software application 400 is run on the remote server 240, receiving commands and information from the computer 100 being input by a user. Information from the LMS software application 400 running on the remote server 240 is displayed on a display connected with the computer 100.

Figure 2:
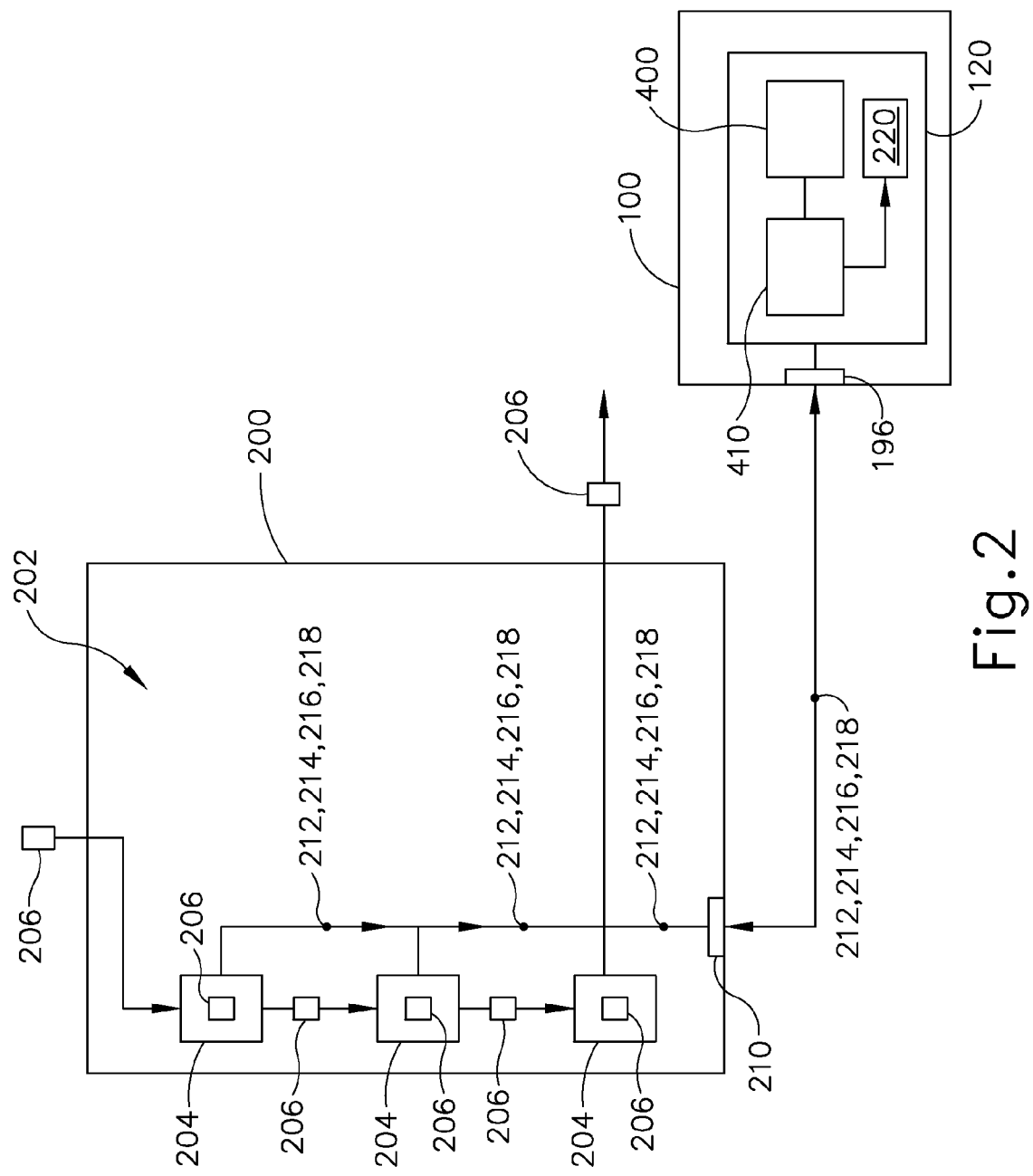
FIG. 2 depicts an illustration of a laboratory with instruments connected with a computer running a laboratory management system, in accordance with one embodiment of the present invention.

With reference to FIG. 2, a graphical display module 410 is provided for graphically generating an instrument information representation 220 in response to receiving information 212 generated by an instrument 204. The graphical display module 410 is connected with or runs within a laboratory management system (LMS) software application 400 used to manage a laboratory 200. Laboratory 200 is any place of manufacture or place of analyses where actions or tests are performed on samples 206 using equipment or instruments 204. Laboratory 200 includes various types of laboratories such as medical or clinical laboratories, biological laboratories, chemistry laboratories, chemical or petroleum laboratories, commercial or manufacturing plants, forensics or crime laboratories, pathology laboratories, public safety and public health laboratories, and water processing and testing facilities. Samples 202 are any object which enters a laboratory 200 upon which an action or test is performed. Samples 202 include: biological samples taken from a patient, such as blood, urine or tissue; evidence samples taken from a crime scene, such as bullets, biological samples, pictures, and video; samples of materials, liquids, or compounds; and parts or components. Instruments 204 are any type of equipment which can perform an action or an analyses or test on a sample 206, and include laboratory instruments, manufacturing equipment such as welding tools and robotic arms, sensors such as temperature sensors and weight sensors, and imaging equipment such as bar code scanners or cameras.

As the instruments become operational and as samples 206 are routed in and out of the laboratory 200, information 212 may be generated by the instrument 204 and transmitted to the LMS software application 400. Information 212 may include: status information 214 which details the status of an instrument 204 including any error messages received from an instrument 204 and any information as to the current operating state of an instrument 204; instrument information which includes information describing the instrument such as the type and model number of the instrument 204; the current workload of an instrument 204 which includes how many jobs an instrument 204 may have in its queue; quality control (QC) information 216 generated by the instrument 204 for QC samples, and results information 218. An instrument information representation 220, as discussed herein, may display real time QC status of each assay performed on an instrument 204. If any assay fails any QC rules defined in the LMS software application 400 using, for example, Westguard Rules, Custom Rules or Moving Average Rules will be applied to QC information 216 and displayed by the instrument information representation 220 so that a user will be alerted as to a failure of the instrument 204 and the user will be able to view in real time the QC information 216 on a display.

As samples 206 are routed to a particular instrument 204 within the laboratory 200, tests or actions are performed on the sample 206, and results information 218 associated with the sample 206 may be generated by the instrument 204 and transmitted to the LMS software application 400. Results information 218 is generated by an instrument 204 in the laboratory 200 and is associated with or is from performing a test or action on the sample 206, and includes things as test results or sample properties, and any other information 208 which may be associated with the sample 206 and obtained from the sample 206 by the instrument 204. Results information 218 is eventually entered into a database managed by the LMS software application 400.

With reference to FIGS. 4-8, LMS software application 400, may display the instrument information representation 220 generated by the graphical display module 410 on a display. The instrument information representation 220 visually presents to a user the information 212 generated by the instrument 204. The instrument information representation 220 may be visually presented in a number of ways, such as by generating an icon or symbol 236, a gauge, a chart 232 or a graph 230 displaying instrument usage, instrument quality control results, or instrument status. The icon 236 may include various different symbols, colors, shades, or patterns, to convey the information 212 received by the instrument 204. For example a "!" symbol within a red circle may be used to convey that an error message has been received from the instrument 204 in instrument information 212.

A gauge may also be used to visually present the information 212 generated by the instrument 204. The gauge may be a moving needle on a dial, or some sort of digital display of information 212. Chart 232 presents information 212 generated by the instrument 204 in a chart or table and graph 230 presents the information 212 generated by the instrument 204 within a graph.

The instrument information representation 220 represented by icon or symbol 236, the gauge, the chart 232 or the graph 230 may be an instrument usage representation displaying instrument usage or other information about instrument 204, an instrument quality control representation 224 displaying instrument quality control results, or an instrument status representation 222 displaying instrument status.

Figure 4:
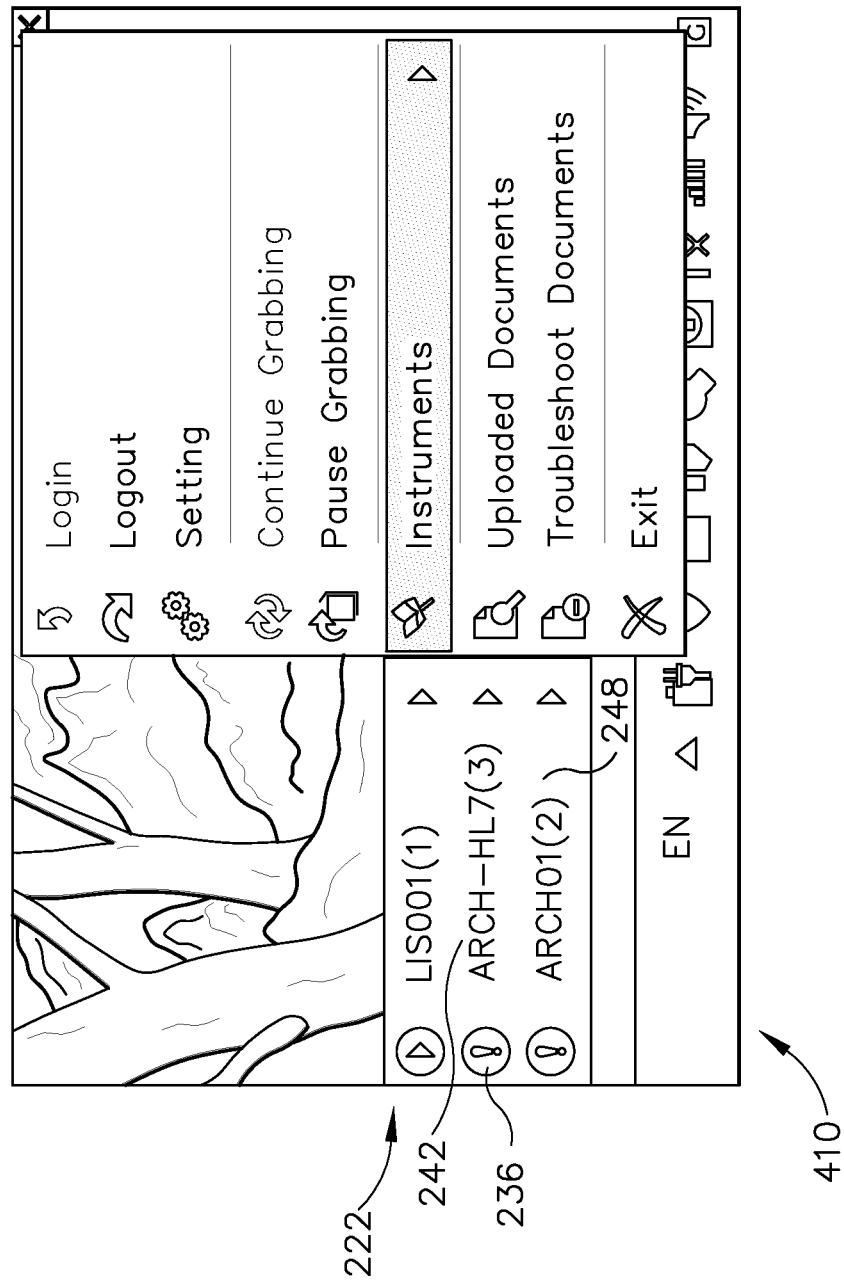
Figure 5:
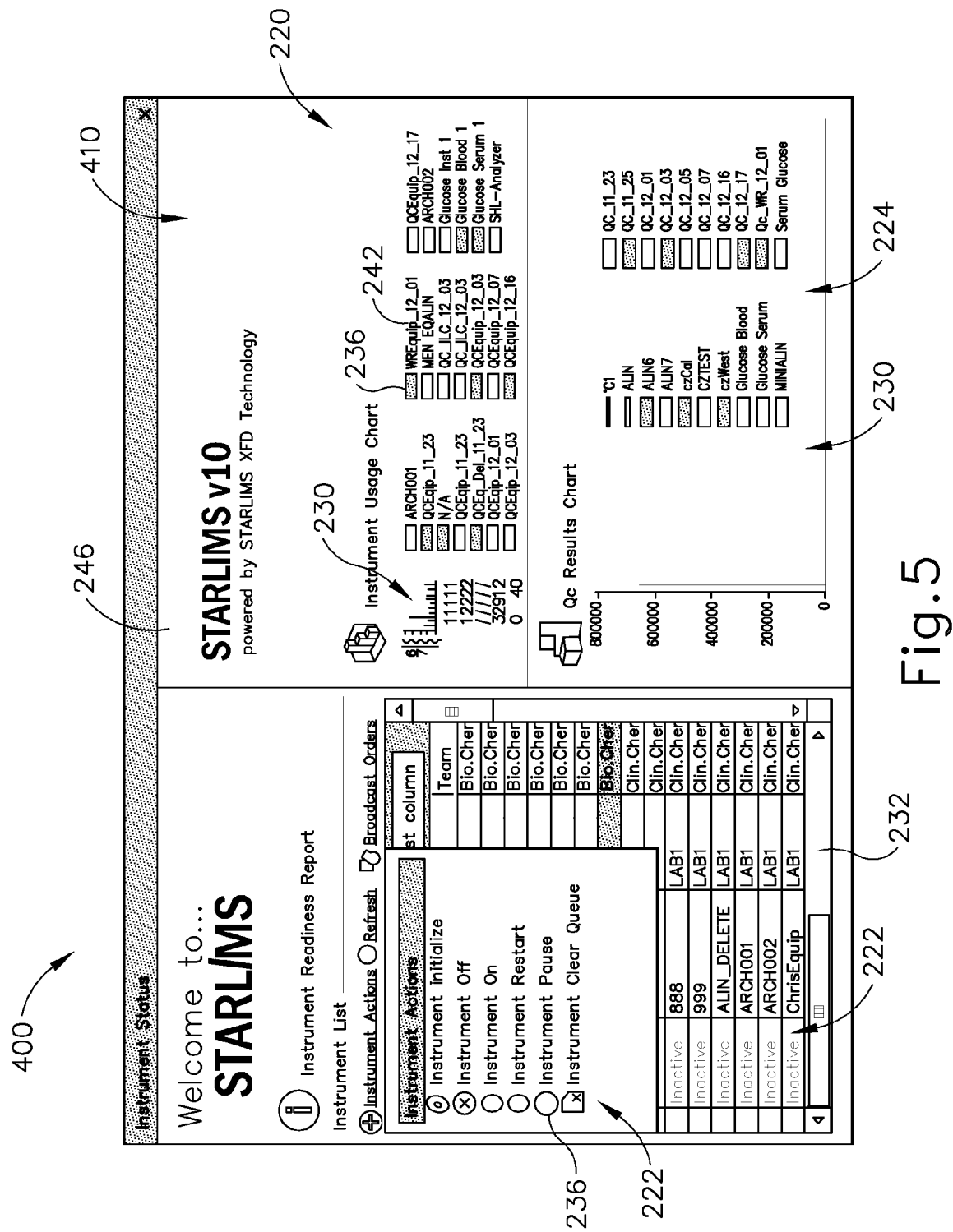

With reference to FIGS. 4 and 5, in one embodiment, the graphical display module 410 may generate an instrument status representation 222 in response to receiving status information 214 generated by the instrument 204. The instrument status representation 222 visually indicates the instrument status of the instrument 204. Upon generating the instrument status representation 222, the graphical display module 410 then displays the instrument status representation 222 on a display.

With reference to FIGS. 5, 7 and 8, in one embodiment, the graphical display module 410 may generate an instrument quality control (QC) representation 224 in response to receiving quality control information 216 generated by the instrument 204. The instrument QC representation 224 visually displays quality control results of the instrument 204. Upon generating the instrument QC representation 224, the graphical display module 410 then displays the instrument QC representation 224 on a display.

With reference to FIGS. 4 and 5, preferably, the display of the instrument information representation 220 is within a window pane 246 or a menu 248 of the laboratory management system 400 to allow a user to more simply view the instrument information representation 220.

With reference to FIGS. 4-6, in one embodiment, the instrument information representation 220 includes the icon or symbol 236, the gauge, the chart 232 or the graph 230 adjacent an instrument representation 238. The instrument representation 238 is any visual representation of the instrument 204 on a display, and includes things such as a textual description 242 of the instrument 204, as shown in FIG. 4, or a graphical depiction 244 of the instrument 204, as shown in FIG. 6.

With reference to FIG. 5, preferably, an instrument information representation 220 is generated for a plurality of instrument 204 or each instrument 204 in the laboratory 200. This allows the user to quickly scan the instrument information representation 220 and see information 212 pertaining to a plurality of instruments 204 within the laboratory.

Figure 3:
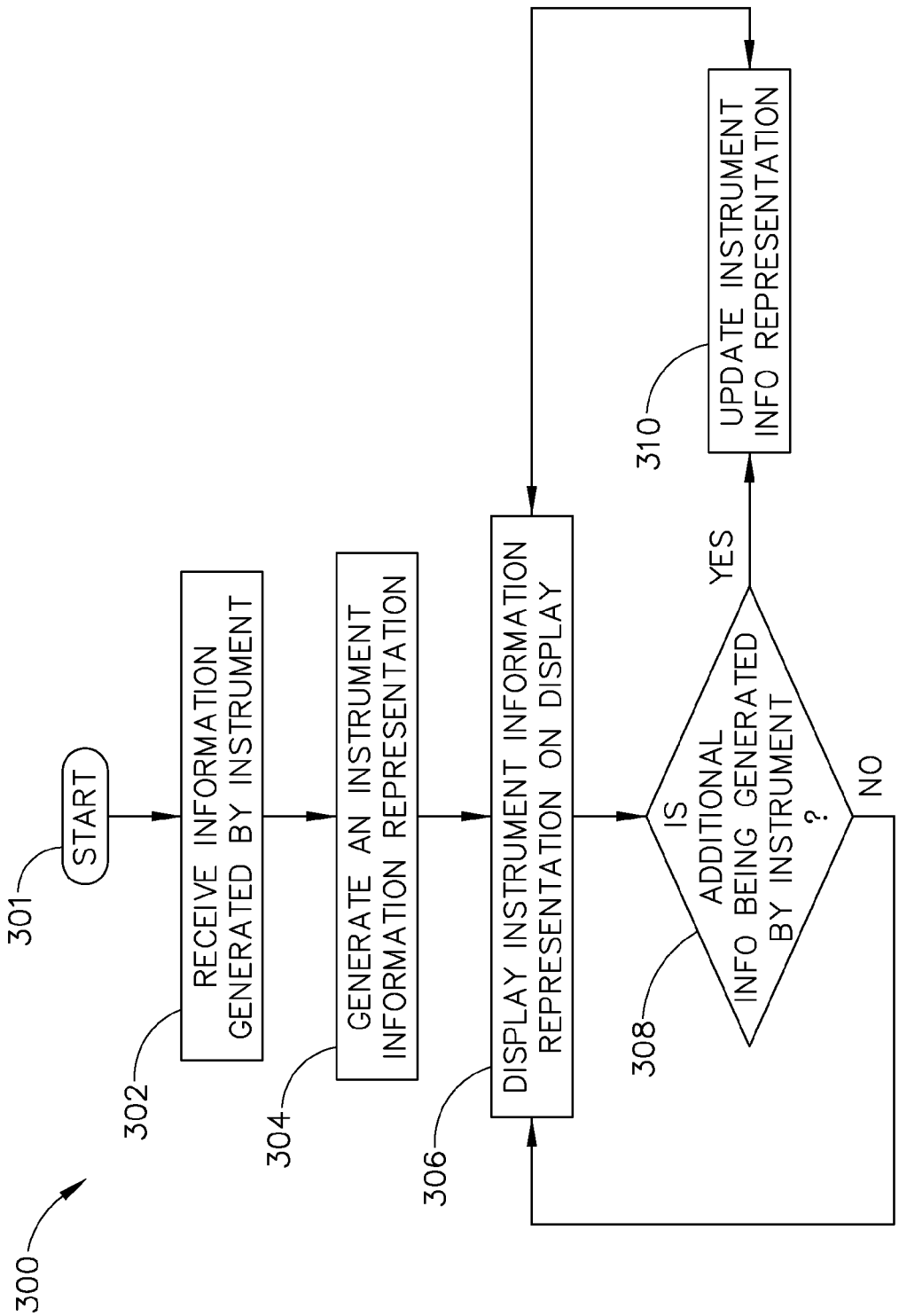
FIG. 3 depicts flowchart illustrations of methods, apparatus (systems) and computer program products, in accordance with one embodiment of the present invention.

Instrument information representation 220 is generated by the graphical display module 410, as shown in FIGS. 4-8. With reference to FIG. 3, is a flowchart representation of a method 300 for graphically displaying information 212 generated by an instrument 204, the information 212 being displayed within a laboratory management system 400. Method 300 is initiated at block 301 by launching LMS software application 400 within the computer 100 or the remote server 240. Concurrent with the launching the LMS software application 400, graphical display module 410 is also launched which resides within or is connected with the LMS software application 400. At block 302, upon launching the LMS software application 400 and within the graphical display module 410, the graphical display module begins to receive information 212 generated by the instrument 204.

Moving to block 304, upon receiving the information 212 generated by the instrument 204, the graphical display module 410 generates an instrument information representation 220 in response to receiving information 212 generated by the instrument 204. The instrument information representation 220 is to be displayed within the laboratory management system software application 400. The instrument information representation 220 visually presents the information 212 generated by the instrument 204 in a more presentable manner so that, so that a user of the LMS software application 400 may glance at the instrument information representation 220 and more easily process or understand the information 212.

Moving to block 306, upon generating the instrument information representation 220, the instrument information representation 220 is then displayed on a display and preferably displayed within the LMS software application 400, as shown in FIG. 5.

Moving to block 308, upon displaying the instrument information representation 220, the graphical display module 410 determines if additional information 212 is being generated by the instrument 204. If additional information 212 is being generated, then method 300 moves to block 310 and upon receiving the additional information 212, the graphical display module 410 updates the instrument information representation 220 when the additional information 212 is received and then moves to block 306 and displays an updated instrument information representation 220. If no additional information is presented, the graphical display module 410 moves to block 306 and continues to display the instrument information representation 220, until the LMS software application 400 is terminated or the user no longer wishes to see the instrument information representation 220, whereby the method 300 ends.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats.

However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a computer readable memory medium such as a magnetic medium like a floppy disk, a hard disk drive, and magnetic tape; an optical medium like a Compact Disc (CD), a Digital Video Disk (DVD), and a Blu-ray Disc; computer memory like random access memory (RAM), flash memory, and read only memory (ROM); and a transmission type medium such as a digital and/or an analog communication medium like a fiber optic cable, a waveguide, a wired communications link, and a wireless communication link.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" or "connected with" each other such that the desired functionality is achieved, irrespective of architectures or intermediate components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. Accordingly, the invention is not to be restricted except in light of the appended claims and their equivalents.

The invention claimed is:

1. A non-transitory computer readable memory medium comprising program instructions for graphically displaying information generated by a plurality of laboratory instruments, the information being displayed within a laboratory management system, wherein the program instructions are executable by a processor to:
   generate instrument information representations for a plurality of laboratory instruments within a laboratory in response to receiving status information generated by an instrument of the plurality of laboratory instruments, wherein each instrument information representation of the plurality of laboratory instruments includes an instrument usage representation, an instrument actions representation, and an instrument quality control representation, the instrument representation visually presenting the information generated by the laboratory instrument, wherein:
      the instrument usage representation indicates a current instrument usage for the plurality of instruments;
      the instrument actions representation for a selected instrument of the plurality of instruments, indicates whether:
         the selected instrument is initialized;
         the selected instrument is on; and/or
         the selected instrument is paused;
      the instrument quality control representation indicates a quality control status of a selected instrument of the plurality of instruments;
   wherein the instrument usage representation, the instrument actions representation, and the instrument quality control representation, are displayed in real time; and
   display each instrument information representation on a display.

2. The computer readable memory medium of claim 1 further comprising program instructions executable by a processor to:
   generate an instrument information representation for a plurality of laboratory instruments for displaying information pertaining to a plurality of laboratory instruments within a laboratory.

3. The computer readable memory medium of claim 2 further comprising program instructions executable by a processor to:
  generate an instrument status representation in response to receiving status information generated by the instrument, wherein the instrument status representation visually indicates instrument status of the instrument; and
  display the instrument status representation on the display.

4. The computer readable memory medium of claim 2 further comprising program instructions executable by a processor to:
  generate an instrument quality control representation in response to receiving quality control information generated by the instrument, wherein the instrument quality control representation visually displays quality control results of the instrument; and
  display the instrument quality control representation on the display.

5. The computer readable memory medium of claim 1, wherein the instrument information representation is a gauge, a chart or a graph displaying instrument usage, instrument quality control results, or instrument status.

6. The computer readable memory medium of claim 1, wherein the display of the instrument information representation is within a window pane or a menu of the laboratory management system.

7. The computer readable memory medium of claim 1, wherein the instrument information representation is an icon, a chart, a graph or symbol adjacent an instrument representation.

8. The computer readable memory medium of claim 7, wherein the instrument representation is a textual description of the instrument or a graphical depiction of the instrument.

9. The computer readable memory medium of claim 1, wherein an instrument information representation is generated for each instrument in the laboratory.

10. The computer readable memory medium of claim 1 further comprising program instructions executable by a processor to update the instrument information representation when additional information generated by the instrument is received.

11. A method for graphically displaying information generated by a plurality of laboratory instruments, the information being displayed within a laboratory management system, comprising:
  generating instrument information representations for a plurality of laboratory instruments in response to receiving status information generated by an instrument of the plurality of laboratory instruments, wherein each instrument information representation visually presents the information generated by one or more laboratory instruments, wherein each instrument information representation includes:
    a current instrument usage,
    an instrument quality control representation displaying the laboratory instrument's quality control status;
    an instrument actions representation for a selected instrument of the plurality of instruments, indicating whether:
      the selected instrument is initialized;
      the selected instrument is on; and/or
      the selected instrument is paused;
  displaying multiple instrument information representations on a display, wherein the current instrument usage, the instrument quality control representation, and the instrument actions representation, are displayed in real time.

12. The method of claim 11, wherein the information generated by the instrument is status information, quality control information, or results information.

13. The method of claim 11 further comprising:
  generating an instrument status representation in response to receiving status information generated by the instrument, wherein the instrument status representation visually indicates instrument status of the instrument; and
  displaying the instrument status representation on the display.

14. The method of claim 11 further comprising:
  generating an instrument quality control representation in response to receiving quality control information generated by the instrument, wherein the instrument quality control representation visually displays quality control results of the instrument; and
  displaying the instrument quality control representation on the display.

15. The method of claim 11, wherein the instrument information representation is an icon, a chart, a graph or symbol adjacent an instrument representation.

16. A laboratory management system comprising:
  a non-transitory computer readable memory medium; and
  at least one processor operable to access from the computer readable memory medium program instructions executable by the processor to:
  generate instrument information representations for a plurality of laboratory instruments in response to receiving status information generated by an instrument of the plurality of laboratory instruments, wherein each instrument information representation visually presents the information generated by at least one laboratory instrument, wherein the instrument information representation includes:
    an instrument usage representation displaying current instrument usage,
    an instrument actions representation for a selected instrument of the plurality of instruments, indicating whether:
      the selected instrument is initialized;
      the selected instrument is on; and/or
      the selected instrument is paused;
    an instrument quality control representation indicating a quality control status of a selected instrument;
    wherein the instrument usage representation, the instrument actions representation, and the instrument quality control representation, are displayed in real time; and
  display each instrument information representation on a display.

17. The laboratory management system of claim 16, wherein the information generated by the instrument is status information, quality control information, or results information.

18. The laboratory management system of claim 16 further comprising program instructions executable by a processor to:
  generate an instrument status representation in response to receiving status information generated by the instrument, wherein the instrument status representation visually indicates instrument status of the instrument; and
  display the instrument status representation on the display.

19. The laboratory management system of claim 16 further comprising program instructions executable by a processor to:
- generate an instrument quality control representation in response to receiving quality control information generated by the instrument, wherein the instrument quality control representation visually displays quality control results of the instrument; and
- display the instrument quality control representation on the display.

20. The laboratory management system of claim 16 further comprising program instructions executable by a processor to update the instrument information representation when additional information generated by the instrument is received.

* * * * *